United States Patent [19]

Chang et al.

[11] Patent Number: 5,817,593

[45] Date of Patent: Oct. 6, 1998

[54] CATALYST AND PROCESS FOR PRODUCING AMINES

[75] Inventors: Dane Chang, Sugar Land; Fred A. Sherrod, Lake Jackson, both of Tex.

[73] Assignee: The Dow Chemical Company, Midland, Mich.

[21] Appl. No.: 459,892

[22] Filed: Jun. 2, 1995

[51] Int. Cl.⁶ .................................................. B01J 21/02
[52] U.S. Cl. ......................... 502/207; 502/104; 502/113; 502/202; 502/203; 502/204; 502/205; 502/206; 564/470; 564/474; 564/477; 564/480
[58] Field of Search .................................. 502/202, 203, 502/204, 206, 207, 104, 113, 205; 564/470, 474, 477, 480

[56] References Cited

U.S. PATENT DOCUMENTS

| | | | |
|---|---|---|---|
| 3,151,115 | 9/1964 | Moss et al. | 260/268 |
| 3,270,059 | 8/1966 | Winderl et al. | 260/583 |
| 3,383,417 | 5/1968 | Lichtenwalter | 260/584 |
| 3,520,933 | 7/1970 | Adam et al. | 260/585 |
| 3,654,370 | 4/1972 | Yeakey | 260/584 B |
| 4,014,933 | 3/1977 | Boettger et al. | 260/563 R |
| 4,111,840 | 9/1978 | Best | 252/432 |
| 4,123,462 | 10/1978 | Best | 260/585 B |
| 4,152,353 | 5/1979 | Habermann | 260/585 B |
| 4,206,149 | 6/1980 | Slaugh | 260/583 R |
| 4,400,539 | 8/1983 | Gibson et al. | 564/480 |
| 4,404,405 | 9/1983 | Winters | 564/482 |
| 4,588,840 | 5/1986 | Gurgiolo | 564/443 |
| 4,634,502 | 1/1987 | Callahan et al. | 204/23 |
| 4,647,701 | 3/1987 | Gibson et al. | 564/512 |
| 4,701,434 | 10/1987 | Köll | 502/230 |
| 4,772,750 | 9/1988 | Habermann | 564/472 |
| 4,775,696 | 10/1988 | Prada-Silva et al. | 518/714 |
| 4,855,275 | 8/1989 | Suresh et al. | 502/353 |
| 4,855,505 | 8/1989 | Köll | 564/398 |
| 4,886,772 | 12/1989 | Prada-Silva et al. | 502/200 |
| 4,967,005 | 10/1990 | Smith | 564/475 |
| 4,973,692 | 11/1990 | Burgess et al. | 544/398 |
| 4,973,761 | 11/1990 | Schoenleben et al. | 564/475 |
| 4,975,399 | 12/1990 | Gardner | 502/439 |
| 4,977,266 | 12/1990 | Burgess et al. | 544/398 |
| 4,992,590 | 2/1991 | Cuscurida et al. | 564/505 |
| 5,003,107 | 3/1991 | Zimmerman et al. | 564/475 |
| 5,068,329 | 11/1991 | Burgess et al. | 544/502 |
| 5,068,330 | 11/1991 | Burgess et al. | 544/402 |
| 5,068,444 | 11/1991 | Cuscurida et al. | 564/505 |
| 5,103,062 | 4/1992 | Curcurida et al. | 564/479 |
| 5,112,364 | 5/1992 | Rath et al. | 44/418 |
| 5,169,971 | 12/1992 | Inomata et al. | 558/338 |
| 5,196,588 | 3/1993 | Burgess et al. | 564/480 |
| 5,202,490 | 4/1993 | Burgess et al. | 564/480 |
| 5,202,491 | 4/1993 | Burgess et al. | 564/480 |
| 5,292,983 | 3/1994 | Sie | 585/733 |
| 5,321,160 | 6/1994 | Hironaka et al. | 564/480 |
| 5,331,101 | 7/1994 | Habermann | 564/480 |
| 5,362,913 | 11/1994 | Knifton et al. | 564/480 |
| 5,424,387 | 6/1995 | Sheehan et al. | 528/61 |
| 5,516,342 | 5/1996 | Cherpeck | 44/347 |

FOREIGN PATENT DOCUMENTS

| | | |
|---|---|---|
| 0 075 940 A1 | 4/1983 | European Pat. Off. . |
| 0 181 140 A2 | 5/1986 | European Pat. Off. . |
| 0 356 725 A1 | 3/1990 | European Pat. Off. ........ C08G 65/32 |
| 0 691 157 A1 | 10/1996 | European Pat. Off. ........ B01J 23/72 |
| 1 569 714 | 6/1980 | United Kingdom ............ B01J 23/84 |
| 2 066 690 | 7/1981 | United Kingdom . |
| 85/00620 A1 | 2/1985 | WIPO .............................. C10L 1/32 |

OTHER PUBLICATIONS

Chemical Abstract 116:87098y (DE 4,114,924) (1992).
Derwent Abstract 35440S (DT 1943213) (1971).
C. M. Barnes and H. F. Rase, "Ethylendiamine by Low–Pressure Ammonolysis of Monethanlamine", *Ind. Eng. Chem. Prod. Res. Dev.* 1981, 20, 399–407.
H. Schaper, et al., "The Influence of Lanthanum Oxide on the Thermal Stability of Gamma Alumina Catalyst Supports", *Applied Catalysis,* 7 (1983) 211–230.

*Primary Examiner*—Peter O'Sullivan

[57] ABSTRACT

This invention includes catalysts comprising rhenium (atomic number 75), nickel, cobalt, boron and copper and/or ruthenium impregnated on a support material and a process for preparing said catalyst, said process comprising (i) impregnating a mixture of metals comprising rhenium, cobalt, copper and/or ruthenium, boron and nickel on a support material selected from the group consisting of alpha-alumina, silica, silica-alumina, kieselguhrs or diatomaceous earths, and silica-titanias; and (ii) activating said catalyst by heating the catalyst in the presence of hydrogen at an effective temperature preferably in the range of about 150° C. to about 500° C. for a sufficient period preferably of from about 30 minutes to about 6 hours. A further feature of the present invention is a method for producing amine products by the catalytic amination of alkane or arylalkane derivatives including epoxides, monols, diols, polyethers, polyols, alcoholamines, ketones, imino compounds iminoalcohols, ether alcohols, and mixtures thereof, said process comprising contacting said lower alkane or arylalkane derivatives with ammonia and/or reactant amine at an effective temperature preferably from 150° C. to about 500° C. and in the presence of hydrogen and the nickel-rhenium-cobalt-boron-copper and/or ruthenium catalyst as described hereinabove.

24 Claims, No Drawings

CATALYST AND PROCESS FOR PRODUCING AMINES

This invention relates to production of amines, more specifically production of amines by reductive amination and catalysts used therein.

Reductive amination is known in the art and is catalytic amination of aliphatic alkane derivatives such as mono-and poly-hydric alcohols, alcoholamines, and compounds from which these alcohols are derived, including epoxides, ketones and alkyleneimines under reducing conditions, preferably in the presence of hydrogen.

The more desirable amine products are those products in which an amine group replaces the non-amine functional group or groups in the alkyl starting material. Heavier, more highly substituted amines and heterocyclic nitrogen compounds can be further synthesized from the preferred alkylamines. These heavier amines are usually less desirable by-products.

Reductive amination is exemplified by the commercial amination of monoethanolamine with ammonia in the presence of a hydrogenation catalyst to produce ethylenediamine. The reaction unavoidably generates a variety of polyalkylene polyamines by-products as well. While any one process may not generate all of these, illustrative polyalkylene polyamines include:

AEEA-N-(2-aminoethyl)ethanolamine
HEP-N-(2-hydroxyethyl)piperazine
DETA-Diethylenetriamine
PIP-Piperazine
AEP-N-(2-aminoethyl)piperazine
TETA-Triethylenetetraamine
TEPA-Tetraethylenepentaamine
PEHA-Pentaethylenehexaamine
TETA Isomers:
NTEA-Nitrilotrisethylamine
TETA-Triethylenetetraamine
DIAEP-Diaminoethylpiperazine
PEEDA-Piperazinoethylethylenediamine
TEPA Isomers:
AETETA-4-Aminoethyltriethylenetetraamine
TEPA-Tetraethylenepentaamine
AEPEEDA-Aminoethylpiperazinoethylethylenediamine
PEDETA-Piperazinoethyldiethylenetriamine The by-products, particularly cyclic amines, like piperazine and aminoethylpiperazine are of less commercial value than ethylenediamine. Furthermore, formation of the by-products consumes the desired ethylenediamine and results in product separation difficulties. A common way to avoid the formation of cyclic amines has been to reduce the overall ethylenediamine yields. High selectivity has been associated with low conversion rates of MEA to product.

Another approach has been to develop catalysts which are more selective while maintaining a rather high conversion rate of MEA. For instance, Burgess et al. in U.S. Pat. No. 5,196,588 disclosed a catalyst having nickel and rhenium in an atom ratio of from 2:1 to 30:1 on a support in an amount corresponding to 3–30 percent by weight of the support material. Various other metals were reported to optionally be present in the catalyst for effects on activity or life of the catalyst. For instance, the presence of boron was reported to have a beneficial effect on the activity of a Ni-Re-B catalyst in Example 7. But in Example 9 boron was reported not to be essential for selectivity or activity, that it "may play a role in the life" of a Ni-Re-Co-B catalyst.

Amine products produced in accordance with the present invention have many uses. In addition to their use as intermediates for synthesizing other chemical materials, they are utilized, for example, in fungicides, insecticides, fuels, detergents, lube oil dispersants, chelants and others.

It would be desirable to have a catalyst which has the ability to obtain high selectivity in the desired products produced yet maintain good amination conversion rates, preferably either greater conversion rates or selectivity toward the product having only replacement of the active functional group by an amine group (EDA, in the case of MEA as starting material) than is shown by the nickel-rhenium catalysts in the art.

SUMMARY OF THE INVENTION

This invention includes catalysts comprising rhenium (atomic number 75), nickel, cobalt, boron and copper and/or ruthenium impregnated on a support material, preferably selected from alpha-alumina, silica, silica-aluminas, kieselguhrs or diatomaceous earths and silica-titania, wherein, preferably the weight ratio of the nickel to the rhenium is in the range of from 1 to about 30; the weight ratio of the nickel to the cobalt is from about 1 to about 20; the weight ratio of the nickel to the boron is from about 1 to about 20; the weight ratio of the nickel to the copper and/or ruthenium is from about 1 to about 20; and the total nickel, rhenium, cobalt, boron plus copper and/or ruthenium metal present is preferably in the range of from about 5 to about 30 percent by weight of the support.

Another feature of the present invention is a process for preparing said catalyst, said process comprising (i) impregnating a mixture of metals comprising rhenium, cobalt, copper and/or ruthenium, boron and nickel on a support material preferably selected from the group consisting of alpha-alumina, silica, silica-alumina, kieselguhrs or diatomaceous earths, and silica-titanias; and (ii) activating said catalyst by heating the catalyst in the presence of hydrogen at an effective temperature preferably in the range of about 150° C. to about 500° C. for a sufficient period preferably of from about 30 minutes to about 6 hours.

A further feature of the present invention is a process for producing amine products by the catalytic amination of alkane or arylalkane derivatives including epoxides, monols, diols, polyethers, polyols, alcoholamines, ketones, imino compounds iminoalcohols, ether alcohols, and mixtures thereof, said process comprising contacting said alkane or arylalkane derivatives with ammonia and/or reactant amine at an effective temperature preferably from about 150° C. to about 500° C. and in the presence of hydrogen and the nickel-rhenium-cobalt-boron-copper and/or ruthenium catalyst as described hereinabove.

It has been found that these catalysts not only exhibit excellent conversion activity but at the same time have superior selectivity in the production of greater amounts of desired amine products yet comparatively smaller quantities of less desired by-products. Furthermore, the catalysts advantageously permit use of less hydrogen and/or ammonia or amine than is commonly used to achieve the same activity and selectivity. The catalysts of the present invention are hydrogenation catalysts and are optionally used in other processes in addition to amination processes.

The catalysts of this invention possess a wide spectrum in magnitude of catalytic activity; can be used in relatively small concentrations; permit the use of a better balance of reactants; and enable the use of reasonable reaction conditions for carrying out the processes.

Advantageously, by controlling certain variables both in the preparation of the catalyst and in the catalytic amination process itself, the activity and selectivity of the amination reaction can be even further optimized and improved.

It has additionally been discovered that the catalysts of the present invention have good selectivity in the amination of a wide range of alkane derivatives including, for example, epoxides, monohydric and polyhydric alcohols, ketones, alkaneimines and aminoalcohols while maintaining good activity in producing the desired products.

DETAILED DESCRIPTION OF THE INVENTION

Reductive amination of alcohols involves a reaction between ammonia and/or amines and alcohols in the presence of hydrogen gas. The amination process consists of a series of hydrogenation and dehydrogenation catalytic reactions. The mechanism of these various reactions have been extensively discussed in the prior art literature. The first step in the amination process is believed to be a reversible dehydrogenation of the alcohol to give an intermediate carbonyl, commonly an aldehyde. The aldehyde is then converted to an aminoalcohol by reaction with ammonia or an amine present in the reaction mixture. The aminoalcohol then loses water to form the imine. The imine is then hydrogenated to the amine. When the intermediate aldehyde or the imine reacts with amines in the reaction mixture, substituted and heavier amines are formed. Alcohols and substituted alcohols are preferred alkane derivative starting materials for practice of the invention.

For convenience in the description of the invention hereinbelow, the amination of monoethanolamine (MEA) to ethylenediamine (EDA) and other products will be most comprehensively discussed, although the present invention is not limited to these starting materials.

The alkane or arylalkane derivatives which can be aminated in the practice of the present invention include alkane and arylalkane derivatives having one or more functional groups. Preferred alkane derivatives include those containing from about one to about 300 carbon atoms, more preferably from 1 to about 100 carbon atoms. Preferred arylalkane derivatives include those having from about 6 to about 300, more preferably from about 7 to about 100 carbon atoms. The functional groups present are suitably on primary, secondary or tertiary carbon atoms. At least one of the functional groups present is capable of being replaced by an amine group (e.g. $NH_2$ from ammonia) in the catalytic amination process of the present invention. The preferred functional groups include hydroxy, amino, imino groups and combinations of said groups. Illustrative examples of preferred alkane derivative starting materials include ethanol, ethylene-glycol (ethanediol), monoethanolamine, ethyleneimine, isopropanol, propanolamines, propanediols, polyols, polyethers, polyether polyols, acetone, butanols, butanediols, aminobutanols, pentanols, pentanediols, aminopentanols, hexanols, hexanediols and aminohexanols. Illustrative examples of preferred arylalkane derivative starting materials include aryl ether derivatives of the preferred alkane starting materials, polyarylether polyols, aryl methyl ether, aryl ethyl ether, aryl propyl ether, aryl butyl ether, aryl pentyl ether, aryl. The aryl groups are suitably of any size and composition that does not interfere undesirably with the amination reaction, preferably of from about 5 to about 30 carbon atoms, more preferably of from about 6 to about 12 carbon atoms, most preferably phenyl or substituted phenyl including methylphenyl, dimethylphenyl, trimethylphenyl, ethylphenyl, diethylpheny, methyl ethylphenyl, propylphenyl, methoxyphenyl, ethoxyphenyl and the like. The starting materials contemplated herein also include compounds from which the aforementioned can be derived. Preferably, at least one of the functional groups in the starting material is a hydroxy group. Functional groups which are not commonly replaceable during amination are optionally present in the alkane starting material in combination with or in addition to the replaceable functional groups. For instance, ether or polyether alcohols are converted to corresponding ether or polyether amines.

Selection of a particular alkane or arylalkane derivative starting material to be used, of course, depends upon the particular amine product desired to be produced. The desired aminated product advantageously differs from the alkane starting material by at least one amine group which replaces at least one non-amine functional group or groups present in the starting material. For example, in the production of ethylene diamine, possible starting materials include ethylene glycol and monoethanolamine (MEA).

The alkane or arylalkane is reacted with preferably ammonia, but optionally at least one amine in addition to or instead of the ammonia. Any amine which reacts with the alkane or arylalkane derivative under reaction conditions in the presence of the catalyst is suitably used, but preferably the amine is primary or secondary, preferably having from 1 to about 10, more preferably from 1 to about 6 carbon atoms and preferably from 1 to about 10, more preferably from 1 to about 6 nitrogen atoms. Preferred amines include methyl amine, ethylamine, ethylenediamine, aniline, piperazine, aminoethylpiperazine, diethylenetriamine, triethylenetetraamine, tetraethylenepentaamine, pentaethylenehexaamine, and the like.

The alkane or arylalkane derivatives are aminated in the presence of a catalyst of the invention.

Advantageously, the catalysts are solid catalysts, preferably supported catalysts with the active species provided on the surface of the support through, e.g., coating or impregnation. Support materials are preferably not themselves sufficiently catalytically active to produce high yields of product in a reasonable time. Useful supports are advantageously porous and have surface areas preferably of from about 10 to about 500, more preferably from about 40 to about 200 square meters per gram.

The catalyst is suitably any convenient size or shape, for instance in the form of powders, spherical or conical pellets, extruded strips and the like. The shape of the support usually depends on the shape suited for a particular apparatus used to perform the reaction. Impregnated spherical pellets e.g. ranging in diameter from 1/32 inch to 3/16 inch and extruded strips of a cylindrical-type shape e.g. ranging from 1/32 inch to ½, inch in length are among those useful as supports.

A particular method of impregnating or coating the metals onto a support material commonly has an insignificant effect on the activity or selectivity of the final catalyst in amination processes; however, impregnated catalysts often perform better than coated catalysts. The amount of metal provided on the support material and the nature of the support itself affect or vary the catalytic activity and/or selectivity.

While any support material which results in an active amination catalyst is suitably used in the practice of the invention, support materials are not equivalent in their ability to form active Ni-Co-Cu-B-(Ru)-Re catalysts. For example, carbon supported and silica-magnesia supported Ni-Re-Co-Cu (Ru)-B catalysts using CXC carbon from National Carbon Company even with large surface areas, have reduced catalytic activity in amination reactions. Preferred supports include those based on silicon, aluminum, and/or titanium, preferably based on silica or alumina, particularly alpha-alumina, silica, silica-alumina, kieselguhrs or diatomaceous earths and silica-titania, most preferably silica based.

Even the alpha-alumina, silica, silica-alumina, kieselguhrs or diatomaceous earths and silica-titania support materials are not equivalent. Those supports which form more active catalysts are those which yield optimum amination conversions at less severe reaction conditions, e.g., lower reaction temperatures. Therefore, although the catalyst of the invention on most of these supports shows catalytic activity in the amination reaction, some supports are more preferred because they result in a more active catalyst, that are capable of withstanding more extreme reaction conditions, such as higher reaction temperatures and/or exhibit better selectivity for the desired product.

The actual effectiveness of a material as a support in a catalyst is not predictable in advance, but determining effectiveness is within the skill in the art, for instance by methods disclosed in reductive amination catalyst patents such as U.S. Pat. No. 4,123,462 the pertinent parts of which are hereby incorporated herein by reference. Among the types of preferred supports, there appears to be some relationship between catalytic activity and the amount of surface area of the particular support materials. The relationship is believed to be attributable to reactions which occur on the catalyst surface and are, therefore, affected by adsorption-desorption equilibria of the reaction materials. The activity of a catalyst is, therefore, affected, within certain limits, by varying surface area of the supports and other surface properties including support shape, pore size, and pore volume. In general, greater dispersion of the metals on higher surface area active supports produce more active catalysts.

Among techniques for impregnating the metals onto the support is use of a solution of salts of the metals as a vehicle to impregnate the support.

Any organic or inorganic nickel and rhenium salt which is capable of resulting in metal on the support is suitably used in impregnation solutions. Preferably, the salts are those which breakdown on heating to form gases such as carbonates, acetates, nitrates and the like. Examples of suitable nickel-containing salts are anhydrous and hydrated nickelous nitrate [hydrate: $Ni(NO_3)_2 \cdot 6H_2O$] and nickel acetonyl acetate [$Ni(C_5H_7O_2)_2$] as well as nickel chloride hexahydrate [$NiCl_2.6H_2O$], nickel acetate tetrahydrate [$(CH_3CO_2)2Ni.4H_2O$], nickel perchlorate hexahydrate [$Ni(ClO_4)_2.6H_2O$], nickel sulfate hexahydrate [$NiSO_4.6H_2O$] and the like. Suitable rhenium salts for use in the impregnating solution include ammonium perrhenate (VII) [$NH_4ReO_4$] and rhenium paradioxane [$Re_2O_7 3(C_4H_8O_2)$] and the like. Suitable cobalt salts include cobalt nitrate hexahydrate [$Co(NO_3)_2.6H_2O$], cobalt chloride hexahydrate [$CoCl_2.6H_2O$], cobalt chloride hydrate [$COCl_2.xH_2O$], cobalt carbonate hydrate [$CoCO_3,xH_2O$] and the like. Suitable copper salts include copper nitrate hydrate [$CuNO_3)_2.H_2O$], copper chloride hydrate [$CuCl_2.xH_2O$], copper chloride dihydrate [$CoCl_2.2H_2O$], copper perchloride hexahydrate [$Cu(ClO_4)_2.6H_2O$] and the like. Suitable boron salts include boric acid [$H_3BO_3$], boron oxide [$B_2O_3$] and the like. Suitable ruthenium salts include ruthenium chloride hydrate [$RuCl_3.xH_2O$] and the like. When the salts have limited room temperature solubility, it is advantageous to heat the solvent liquid to bring the metal salts into solution.

Both the amount of total metal desired to be impregnated on a specific quantity of support and the relative atom ratio of the metals affect the final properties of the catalyst.

The most active catalysts have been found to be those in which the Ni/Re atom ratio is between about 1 and about 30, preferably between about 1 and about 10, most preferably between about 2 and about 6. Similarly the Ni/Co atom ratio is preferably between about 1 and about 30, more preferably between about 1 and about 10, most preferably between about 2 and about 6. The Ni/Cu and/or Ni/Ru atom ratio is preferably between about 1 and about 30, more preferably between about 1 and about 10, most preferably between about 2 and about 6. The Ni/B atom ratio is preferably between about 1 and about 20, more preferably between about 1 and about 10, most preferably between about 2 and about 6. The metal atom ratios are obtained by predetermining the corresponding relative proportions of the metal salts to be present in the impregnation solution. These correspond to Ni/Re weight ratios of preferably from about 1 to about 30, more preferably from about 1 to about 10, most preferably from about 2 to about 6; Ni/Co weight ratios of preferably from about 1 to about 30, more preferably from about 1 to about 10, most preferably from about 2 to about 6; Ni/B weight ratios of preferably from about 1 to about 30, more preferably from about 1 to about 10, most preferably from about 2 to about 6; and Ni/Cu and/or Ru weight ratios of preferably from about 1 to about 30, more preferably from about 1 to about 10, most preferably from about 2 to about 6.

The total metal to be impregnated onto the support also has an effect on the activity of the catalyst. A silica or alumina supported catalyst having a high surface area has greater activity with greater amounts of metal present. A silica-alumina supported catalyst with a lower surface area than the silica support sometimes has greater activity with less metal.

Catalysts of the invention, therefore, advantageously have a total nickel plus rhenium plus cobalt plus copper and/or ruthenium plus boron metal content at least sufficient to convert a hydroxyl group to an amine group, preferably at least about 2 percent by weight and preferably less than about 51 percent by weight of combined metals based on weight of support material, more preferably from about 5 to about 30 weight percent, most preferably from about 8 to about 25 weight percent, particularly from about 10 to about 20 percent.

The catalysts include catalysts which contain various other metals in admixture with the nickel, cobalt, copper, and/or ruthenium, rhenium and boron which do not detrimentally affect catalytic properties. These additional metals, in certain amination processes are optionally used to improve selectivity and activity of the catalyst or extend the activity life and other physical properties of the catalyst. Examples of additional metal components include lanthanum, calcium, magnesium, lithium, sodium, potassium, chromium, molybdenum, rubidium, cesium, cerium, iron, silver, zinc, barium, tungsten, uranium, strontium, palladium, titanium, manganese, rhodium and combinations thereof. To prepare such catalysts, salts of these additional metals are added in suitable amounts to the impregnation solution containing the nickel, cobalt, copper and/or ruthenium, rhenium and boron. The amount of such additional metal components, based on nickel and expressed as an atomic ratio, is preferably about 0.001:1 to about 1:1, more preferably about 0.01:1 to about 0.5:1.

Where relatively large amounts of metal are to be impregnated on supports with relatively low surface areas or high densities, a single impregnation step may not be sufficient or optimal, for instance, when an impregnation solution prepared with the minimum amount of solvent required to dissolve the metal salts is more than that which the support material can absorb. In such a case, a portion of the impregnation solution less than the maximum absorption amount is used to first contact the support material. After the first contact, the support material is dried and then contacted with an additional amount of the impregnation solution. The sequential steps of contacting with solution and drying are continued until a predetermined or desirable loading of salt is obtained. A drying step optionally comprises heating the impregnated support to a temperature of e.g. 120° C. for several hours. Evacuation drying where the support is cooled under reduced pressure or other drying methods within the skill in the art are optionally used.

With any method of impregnation, it advantageous to dry the support material prior to impregnation so the support will absorb as much of the solution as possible. This pre-drying step is believed to enable the metal to permeate more deeply into the support during impregnation. The penetration of the metal into the support is optionally further increased by techniques within the skill in the art such as by increasing the time the support is in contact with the solution.

Other impregnation techniques are within the skill in the art and are optionally utilized in the present invention. Another technique useful in the practice of the invention is a coating technique that results in the metals being predominantly present on the outer surface of the support material.

Such a coating technique differs from the impregnation process described previously by the addition of a precipitant when the impregnating salt solution is in contact with the support material. The precipitant converts the metal salt solution into a slurry. This impregnating vehicle reduces the penetration of the salts beyond the surface of the support material. The slurry in contact with the support material is then dried to leave the metal adhering predominantly to the support surface.

After the support material is impregnated or coated with the desired amount of metals, it is advantageously dried and then activated by a reduction step.

Drying is within the skill in the art. The drying step is any technique which sufficiently evaporates the volatile constituents of the impregnating solution to leave active catalyst. The drying step optionally comprises heating the catalyst to a temperature of e.g. about 120° C. Drying is optionally done under an inert atmosphere, such as nitrogen. Then the catalyst is optionally cooled, optionally under reduced pressure.

After being dried, the catalyst is activated by any procedure wherein the impregnated metal is converted into a catalytically active form. This activation optionally includes alloy formation, proper phase orientation of the metals and/or an adjustment in the oxidation level of the metals. An activation step optionally includes a reduction process within the skill in the art. Often the catalyst is first reduced before effecting the reaction, and then continuously reduced during the course of the reaction to keep the catalyst active and functioning. Insufficient reduction results in depletion of hydrogen at the catalyst surface and resulting decreased reaction.

A preferred activation procedure includes use of a hydrogen atmosphere in contact with the catalyst. The hydrogen is advantageously fed over the catalyst at an elevated temperature, preferably on the order of at least about 150° C., more preferably about 350° C. and preferably less than about 600° C., more preferably less than about 500° C. for periods of from about 30 minutes to about 8 hours, more preferably from about 3 hours to less than about 6 hours. Specific conditions for reduction depend on the particular catalyst composition being activated.

Before or during an activation step, the catalyst is optionally calcined. In a preferred calcining step, the catalyst is heated to temperatures of from about 200° C. to about 500° C. for about 45 minutes to about 3 hours or more if convenient. It is preferred that the calcining be carried out in air.

The drying step previously discussed is optionally replaced by a calcining step or activating step. Alternatively, in such cases drying is considered to take place simultaneously with a calcining and/or activating step.

The amount of catalyst preferred for use in the practice of the invention depends on many variables including the relative proportions of the reactants, reaction conditions and the degree of conversion and selectivity desired. Moreover, the amount of catalyst also depends on the catalyst itself, e.g., its metal loading, activity and age. Overall, the amount of catalyst used in the process is an amount sufficient to result in the desired reaction.

Reaction conditions of the amination of alkane derivatives are known in the art, but are somewhat dependent on the activity and other characteristics of the catalyst. Ascertaining optimum conditions for use of each individual catalyst is within the skill in the art. Because the catalyst of the invention improves the conversion of raw material and selectivity of the reaction, reaction conditions are less severe than many found in the art or require less time for equivalent reaction under the same condition.

The reaction is preferably conducted under elevated pressure, advantageously sufficient pressure to maintain desired amounts of hydrogen and ammonia and/or amine present for the reaction at a desired temperature. The reaction occurs in a liquid phase, in a liquid phase including at least some of the alkane starting material and a gas phase, or in a gas phase. For purposes herein, the term gas phase encompasses both the vapor phase and supercritical phase. While it is possible to conduct the process when the reaction mixture contains components both in the liquid and gas phases, it is preferable to use an amination reaction feed stream that is in a homogeneous phase. The processes of this invention are particularly useful in operations in which the amination reaction feed stream is in the gas phase.

The pressure is not critical to operability but is selected for convenience and/or to result in a desired phase or phases at the reaction temperature. Conveniently the pressure is at least about 20 atmospheres (2026 kPa), preferably at least about 500 psig (3447 kPa), more preferably at least about 800 psig (5516 kPa), most preferably at least about 1800 psig (12411 kPa). Preferably the pressure is lower than a pressure which requires unduly heavy equipment or danger, conveniently less than about 400 atmospheres (40,530 pKa). Reaction is suitably maintained in liquid, gas or preferably supercritical fluid state by combination of temperature and pressure.

Preferred temperatures for the reaction depend on the particular starting material, ratios of reactants, and most importantly, the activity of the catalyst used. Temperatures are advantageously at least sufficient to result in reaction and insufficient to result in undesirably increased by-products. Overall, in processes of the invention, such temperatures are advantageously at least about 120° C., preferably at least about 150° C., more preferably at least about 160° C., most preferably at least about 170C. Also, to avoid increased by-products, the temperatures are preferably less than about 250° C., more preferably less than about 225° C., most preferably less than about 200° C.

Such conditions of temperature and pressure are not critical to the practice of the invention. Under these conditions, reactant alkane derivative, ammonia and/or amine and hydrogen are supplied to a reaction zone containing reductive amination catalyst at an elevated temperature sufficient to replace the functional group on the alkane with an amine functional group.

Reactants are optionally fed as a feed stream which is optionally liquid, supercritical fluid or gaseous. Reaction product stream(s) taken from the reaction zone are also optionally liquid, supercritical fluid or gaseous. It is not necessary that the feed stream and the reaction product stream be in the same physical state. For example, a reactant stream is optionally gaseous and a reaction product stream liquid, or vice versa. Feed reactants are suitably supplied in any amount which results in product; conveniently a liquid hourly space velocity (LHSV) (total feed volume divided by volume of reactor containing catalyst per hour) is at least about 0.05 reciprocal hours, advantageously from about 0.05 to about 2, preferably from about 0.1 to about 1.5, more preferably from about 0.25 to about 1, most preferably form about 0.5 to about 0.75 reciprocal hours.

To maintain a given conversion rate, as a reactant alkane derivative feed rates is increased, one or more other process variables are changed; for instance catalytic activity or temperature is increased. Most commonly, a given conversion rate is maintained by an increase in temperature with an increase in e.g. ethanolamine feed rate. Higher temperatures, however, lead to increased by-products; therefore, the LHSV is balanced with the temperature to achieve the optimum result in each situation.

A feed stream to the amination reaction zone comprises reactant alkane or arylalkane derivative, ammonia and/or amine and hydrogen. Although the reactant alkane or arylalkane derivative optionally contains impurities, such as diethanolamine and triethanolamine in the case of MEA, the feed rate is considered herein to be the feed rate of the total ethanolamines or other alkane or arylalkane derivative. Because of the selectivity to ethylenediamine and low production of cyclic amines provided by this invention, when higher amines are desired, it is advantageous to add to the feed amines such as ethylenediamine for conversion to diethylenetriamine or other higher ethyleneamines.

The feed to the reaction zone also comprises ammonia or amine. Stoichiometrically, one molecular unit of ammonia or amine (primary or secondary) is required per molecular unit of functional group, e.g. hydroxyl, to be replaced. However, the formation of linear ethyleneamines is favored by the presence of excess ammonia or amine. Energy consumption gives a practical limit on the amount of ammonia or amine. Thus, the molar ratio of ammonia and/or amine to total ethanolamine or other alkane or arylalkane derivative is advantageously from at least about 2:1 to about 50:1, preferably from about 5:1 to about 40:1, more preferably from about 10:1 to about 25:1, and most preferably 10:1 to 20:1. One advantage of the present invention is that because of the exceptional selectivity of the catalyst of the present invention, only a relatively small excess of ammonia is required. For instance, a molar ratio of 12:1 results in high selectivity for the desired product over cyclic by-products or other products of multiple condensation.

It has been found that increasing the weight ratio of ammonia or amine to the alkane or arylalkane derivative reactant decreases the activity or conversion rate of the reaction in some types of reactors. Excess ammonia or amine is believed to reduce available surface of the catalyst in these instances.

Ammonia or amine employed in the reaction is optionally anhydrous or contains small amounts of water.

Hydrogen is also provided to the amination reaction zone. The amount of hydrogen gas present in the amination process of the present invention is not critical. Advantageously, hydrogen is added in an amount sufficient to maintain the catalyst in an active state. A preferred amination process is carried out where the hydrogen is present in an amount wherein the hydrogen to ammonia molar ratio is greater than 0.005 and preferably less than the ratio 0.1:1. More preferably, hydrogen is provided in an amount of at least about 0.5 mole percent based on the total moles of ammonia, most preferably this percentage is between about 0.75 and about 2.5 percent. Advantageously, catalysts of the invention operate well at lower hydrogen concentrations based on total feed than do commercially available catalysts for reductive amination.

The amination reaction feed stream optionally also contains an amount of water. The water is often that produced when the starting material alkane derivative, e.g. MEA, is formed. The water content in the amination feed stream optionally ranges between 0 weight percent and about 10 or more weight percent, based on the weight of the amination feed stream; preferably the water content is kept between about 0 and about 5 weight percent, based on the total weight of the amination feed stream.

Inert gases are also optionally supplied to the reaction such as nitrogen, helium, methane, and the like. Such inert gases are optionally used to help control the reaction temperature and assist in maintaining a desired pressure.

Processes of the invention are preferably conducted in a continuous manner more preferably with a reactor feed being passed through a bed of particulate catalyst. The reactor is optionally an up-flow or down-flow reactor and optionally has a fluidized bed or, more commonly, a fixed bed. The catalyst bed optionally contains inert particles which are, for instance, interspersed throughout the bed and/or form discrete layers, e.g., at an end or intermediary to the bed. Preferably, flow through a catalyst bed is substantially plug flow.

The reductive amination process of the invention is suitably carried out in any equipment having heating means. The process is optionally carried out continuously or in batch. In continuous equipment no agitating means is required because the nature of the continuous process causes the reactants to continually flow in intimate contact with the catalyst material. Agitating means is, however, advantageous in batch processes.

While the present invention advantageously produces EDA from MEA with particular selectivity, the market for amines sometimes includes a demand for DETA that exceeds that produced by the process of the invention practiced to maximize EDA production and selectivity. When DETA is desired, the process of the invention is advantageously modified by using as at least a portion of the starting material, a recycle stream comprising EDA mixed with water, particularly a water-EDA azeotropic mixture or a water-EDA-PIP mixture. Addition of EDA to the feed stream entering an amination reactor is accomplished in a number of alternative ways: for instance, EDA is optionally supplied from storage to the reactant feed stream; or EDA is optionally recycled from an effluent, e.g. of a still, distillation column or a sidestream. The EDA optionally contains water and/or PIP.

The alkyleneamine product compositions from practice of the invention are optionally subjected to separation techniques within the skill in the art for recovering individual components or fractions of the compositions. Illustrative techniques are disclosed in U.S. Pat. No. 5,196,588 (Burgess et al.), U.S. Pat. No. 4,400,539 (Gibson, et al.), U.S. Pat. No. 4,404,405 (Winters), and U.S. Pat. No. 3,151,115 (Moss, et al.).

Aminoalkane or arylalkamine derivatives conveniently produced by the process of the invention include polyamines, amine derivatives and/or amine capped polyols useful in polyurethanes, epoxy resins, fuel and lubrication additives applications, amine functional chelating compounds useful e.g. in detergent applications and the like. Such compounds include amines having other functional groups such as alkylene or arylene ether amines, polyether polyamines, amino acids, amino esters, amides, amino ketones, amino aldehydes, and the like.

The following examples are to illustrate this invention and not limit it. Ratios, parts, and percentages are by weight unless otherwise stated. Examples (Ex) of the invention are designated numerically while comparative samples (C.S.) are designated alphabetically and are not examples of the invention.

Selectivity is used to indicate mole percent of a product or by-product. Reactivity is used to indicate the mole percent conversion of reactant alkane or arylalkane derivative to products and by-products. It is important to maintain a high selectivity, preferably above about 5, more preferably above about 70, most preferably about 80 mole percent for the desired product as well as a high reactivity, preferably above about 20, more preferably above about 30, most preferably about 40 mole percent conversion.

EXAMPLE 1: ILLUSTRATING THE EFFECTS OF A CATALYST CONTAINING Ni/Co/Cu/Re/B

A 200 ml aqueous solution of 51.97 g of $Ni(NO_3)_2.6H_2O$, 4.49 g of $NH_4ReO_4$, 13.04 g of $H_3BO_3$, 15.21 g of $Co(NO_3)_2.6H_2O$ and 11.27g of $Cu(NO_3)_2.2.5H_2O$ is well mixed at 90° C. A 116 g batch of ⅛-inch silica support commercially available from United Catalyst under the trade designation T-869™ is heated in a 120° C oven for two hours, added to a round bottom flask and kept under moderate vacuum for ten minutes, after which 100 ml of the catalyst solution is slowly added to the support under vacuum. After thorough mixing and evaporation of most of the water, the catalyst is poured into a crucible and dried in an air oven at 120° C. with occasional stirring. The dried catalyst is placed back into the round bottom flask and left under vacuum for ten minutes before the second 100 ml of the solution is slowly added to the catalyst support. After thorough mixing and complete drying at 120° C., the catalyst is calcined at 300° C. for three hours in the air oven, then allowed to cool to room temperature. The resulting catalyst contains a Ni/Co/Cu/Re/B metal weight ratio of 48/14/14/14/10 and the Ni/Co and Ni/Cu weight ratios are 3.4. The total metal loading is about 16 weight percent.

This catalyst is activated in an activation chamber. The temperature of the chamber is slowly heated to 330°±10° C. over a period of about two hours, while a stream of pure hydrogen gas is flowing through the chamber at about 400 ml/min. Activation is continued for 3 hours after the temperature has reached about 330° C. Then the heat is turned off and H2 flow is continued until the chamber has cooled to room temperature. The activated catalyst (pyrophoric) is carefully transferred into a bottle in a $N_2$ filled drybox and stored there until use.

Loading of the catalyst (40 g/50 ml) into a plug-flow having dimensions of 1 inch (25.4 mm) inside diameter and 100 mL capacity, commercially available from Autoclave Engineer rated at 9500 psi (65500 kPa)/5500° F. (260° C.) reactor, is performed inside a $N_2$ filled drybox ($O_2$ less than 10 ppm) to prevent deactivation of the catalyst. Ceramic berl saddle packing (¼") is used above and below the catalyst so the catalyst bed is positioned in the constant temperature zone of the reactor.

The feed rates used are 0.21–0.82 ml/min for MEA, 0.97–15.22 ml/min for $NH_3$, and 10–928 sccm (standard cubic centimeters per minute) for $H_2$, which gives $NH_3$/MEA molar ratios ranging from 10 to 40. Liquid hourly space velocities (LHSV =volume of MEA /volume of catalyst bed /hour) for MEA ranged from 0.25 to 1.0. The reactor temperature range is 160° –190 ° C., and the pressure is maintained at from 2000 to 2600 psig (13790 to 17926 kPa Results are given in Table 1 along with the conditions and amounts of reactants. All samples are analyzed on a commercially available Hewlett-Packard 5890II GC equipped with a Model 7673 autosampler, and a Hewlett-Packard ultra-performance capillary column Ultra 1 (cross-linked methyl silicon gum phase column, 50m×0.32mm×0.52mm).

TABLE 1

| Example Number | conditions Reactor Temperature °C. | pressure psig | pressure kPa | MEA/NH₃/H₂ ml/min | reactants molar ratio NH₃/MEA | LHSV | H₂ mole % of total feed | MEA % conversion | SELECTIVITY In mole % (based on MEA converted) | | | | | | |
|---|---|---|---|---|---|---|---|---|---|---|---|---|---|---|---|
| | | | | | | | | | EDA | PIP | DETA | AEEA | AEP | TETA | THPA |
| 1 | 160 | 2400 | 16547 | 0.21/0.97/22 | 10 | 0.25 | 2.50% | 30.56 | 73.02 | 7.59 | 10.36 | 6.45 | 0.95 | 1.63 | 0.00 |
| 2 | 160 | 2400 | 16547 | 0.21/0.97/64 | 10 | 0.25 | 7.00% | 33.59 | 66.06 | 9.53 | 12.00 | 8.47 | 1.37 | 2.56 | 0.00 |
| 3 | 160 | 2400 | 16547 | 0.21/3.90/83 | 40 | 0.25 | 2.50% | 20.60 | 89.38 | 3.28 | 4.65 | 2.69 | 0.00 | 0.00 | 0.00 |
| 4 | 160 | 2400 | 16547 | 0.21/3.90/238 | 40 | 0.25 | 7.00% | 27.23 | 77.26 | 7.04 | 7.73 | 5.44 | 1.33 | 1.40 | 0.00 |
| 5 | 160 | 2400 | 16547 | 0.82/3.80/85 | 10 | 1.00 | 2.50% | 12.69 | 86.53 | 1.90 | 5.59 | 5.98 | 0.00 | 0.00 | 0.00 |
| 6 | 160 | 2400 | 16547 | 0.82/3.80/249 | 10 | 1.00 | 7.00% | 13.76 | 78.71 | 3.13 | 7.73 | 9.46 | 0.00 | 0.98 | 0.00 |
| 7 | 160 | 2400 | 16547 | 0.82/15.22/316 | 40 | 1.00 | 2.50% | 8.24 | 96.29 | 0.00 | 2.37 | 1.34 | 0.00 | 0.00 | 0.00 |
| 8 | 160 | 2400 | 16547 | 0.82/35.22/928 | 40 | 1.00 | 7.00% | 11.67 | 88.08 | 2.27 | 4.29 | 5.35 | 0.00 | 0.00 | 0.00 |
| 9 | 180 | 2400 | 16547 | 0.21/0.97/22 | 10 | 0.25 | 2.50% | 77.89 | 53.04 | 25.76 | 30.32 | 1.90 | 5.48 | 2.80 | 0.70 |
| 10 | 180 | 2400 | 16547 | 0.21/0.97/64 | 10 | 0.25 | 7.00% | 72.43 | 48.67 | 27.01 | 10.97 | 2.58 | 6.22 | 3.67 | 0.88 |
| 11 | 180 | 2400 | 16547 | 0.21/3.90/81 | 40 | 0.25 | 2.50% | 60.81 | 73.10 | 15.11 | 5.79 | 1.22 | 3.63 | 0.93 | 0.22 |
| 12 | 180 | 2400 | 16547 | 0.21/3.90/238 | 40 | 0.25 | 7.00% | 67.06 | 59.58 | 25.52 | 5.08 | 0.53 | 7.69 | 0.69 | 0.91 |

TABLE 1-continued

| Example Number | Reactor Temperature °C. | conditions pressure psig | pressure kPa | reactants MEA/NH₃/H₂ ml/min | molar ratio NH₃/MEA | LHSV | H₂ mole % of total feed | MEA % conversion | SELECTIVITY In mole % (based on MEA converted) | | | | | | |
|---|---|---|---|---|---|---|---|---|---|---|---|---|---|---|---|
| | | | | | | | | | EDA | PIP | DETA | AEEA | AEP | TETA | THPA |
| 13 | 180 | 2400 | 16547 | 0.82/3.80/85 | 10 | 1.00 | 2.50% | 39.87 | 73.38 | 9.34 | 9.72 | 4.19 | 1.74 | 1.64 | 0.00 |
| 14 | 180 | 2400 | 16547 | 0.82/3.80/249 | 10 | 1.00 | 7.00% | 39.62 | 66.24 | 11.56 | 11.64 | 5.76 | 2.26 | 2.55 | 0.00 |
| 15 | 180 | 2400 | 16547 | 0.82/15.22/316 | 40 | 1.00 | 2.50% | 28.61 | 85.42 | 6.43 | 4.65 | 2.09 | 1.40 | 0.00 | 0.00 |
| 16 | 180 | 2400 | 16547 | 0.82/15.22/928 | 40 | 1.00 | 7.00% | 29.42 | 80.79 | 8.27 | 5.65 | 2.99 | 1.86 | 0.45 | 0.00 |
| 17 | 160 | 2400 | 16547 | 0.41/4.75/193 | 25 | 0.50 | 4.70% | 17.88 | 84.66 | 3.72 | 6.57 | 5.05 | 0.00 | 0.00 | 0.00 |
| 18 | 180 | 2400 | 16547 | 0.41/4.75/193 | 25 | 0.50 | 4.70% | 56.00 | 65.38 | 17.52 | 8.26 | 2.31 | 4.28 | 2.02 | 0.44 |
| 19 | 170 | 2400 | 16547 | 0.21/2.44/99 | 25 | 0.25 | 4.70% | 52.28 | 70.05 | 13.32 | 8.87 | 2.92 | 2.65 | 1.88 | 0.33 |
| 20 | 170 | 2400 | 16547 | 0.82/9.51/386 | 25 | 1.00 | 4.70% | 22.45 | 82.81 | 4.56 | 6.54 | 4.65 | 0.72 | 0.72 | 0.00 |
| 21 | 170 | 2400 | 16547 | 0.41/1.90/82 | 10 | 0.50 | 4.70% | 39.22 | 70.12 | 8.92 | 11.14 | 5.90 | 1.42 | 2.00 | 0.50 |
| 22 | 170 | 2400 | 16547 | 0.41/7.61/304 | 40 | 0.50 | 4.70% | 26.07 | 84.98 | 5.66 | 5.40 | 2.96 | 1.01 | 0.00 | 0.00 |
| 23 | 170 | 2400 | 16547 | 0.41/4.75/100 | 25 | 0.50 | 2.50% | 32.61 | 82.49 | 6.25 | 6.64 | 2.87 | 1.10 | 0.64 | 0.00 |
| 24 | 170 | 2400 | 16547 | 0.41/4.75/294 | 25 | 0.50 | 7.00% | 34.40 | 72.32 | 9.75 | 9.34 | 5.32 | 1.81 | 1.66 | 0.00 |
| 25 | 170 | 2400 | 16547 | 0.41/4.75/193 | 25 | 0.50 | 4.70% | 35.07 | 77.75 | 7.62 | 8.02 | 4.33 | 1.34 | 1.14 | 0.00 |
| 26 | 170 | 2575 | 17754 | 0.41/4.75/300 | 25 | 0.50 | 2.50% | 25.25 | 85.57 | 4.83 | 5.92 | 3.05 | 0.64 | 0.00 | 0.00 |
| 27 | 170 | 2200 | 15168 | 0.41/4.75/100 | 25 | 0.50 | 2.50% | 36.55 | 77.28 | 7.79 | 8.31 | 3.68 | 1.62 | 1.31 | 0.00 |
| 28 | 170 | 2000 | 13790 | 0.41/4.75/100 | 25 | 0.50 | 2.50% | 42.36 | 73.15 | 9.74 | 8.99 | 3.85 | 2.36 | 1.92 | 0.00 |
| 29 | 180 | 2400 | 16547 | 0.41/4.75/100 | 25 | 0.50 | 2.50% | 51.94 | 72.36 | 13.99 | 7.26 | 1.85 | 3.56 | 3.38 | 0.00 |
| 30 | 160 | 2400 | 16547 | 0.41/4.75/100 | 25 | 0.50 | 2.50% | 12.69 | 90.14 | 2.24 | 4.39 | 3.23 | 0.00 | 0.00 | 0.00 |
| 31 | 170 | 2400 | 16547 | 0.41/4.75/294 | 25 | 0.50 | 7.00% | 33.64 | 74.50 | 8.44 | 9.02 | 5.06 | 1.48 | 1.50 | 0.00 |
| 32 | 170 | 2000 | 13790 | 0.41/4.75/294 | 25 | 0.50 | 7.00% | 40.65 | 70.45 | 9.89 | 10.04 | 4.93 | 2.08 | 2.27 | 0.35 |
| 33 | 170 | 2600 | 17926 | 0.41/4.75/294 | 25 | 0.50 | 7.00% | 30.02 | 76.19 | 7.87 | 8.44 | 4.99 | 1.30 | 1.21 | 0.00 |
| 34 | 170 | 2200 | 15168 | 0.41/4.75/294 | 25 | 0.50 | 7.00% | 37.14 | 72.96 | 9.02 | 9.51 | 5.04 | 1.70 | 1.77 | 0.00 |
| 35 | 180 | 2400 | 16547 | 0.41/4.75/294 | 25 | 0.50 | 7.00% | 53.23 | 65.50 | 16.22 | 8.74 | 2.84 | 3.90 | 2.27 | 0.52 |
| 36 | 160 | 2400 | 16547 | 0.41/4.75/294 | 25 | 0.50 | 7.00% | 17.01 | 81.74 | 3.91 | 6.80 | 6.69 | 0.00 | 0.84 | 0.00 |
| 37 | 170 | 2400 | 16547 | 0.41/4.75/90 | 25 | 0.50 | 2.25% | 29.65 | 83.31 | 5.68 | 6.52 | 2.93 | 0.92 | 0.67 | 0.00 |
| 38 | 168 | 2400 | 16547 | 0.41/4.75/100 | 25 | 0.50 | 2.50% | 25.99 | 88.12 | 3.73 | 4.73 | 2.86 | 0.56 | 0.00 | 0.00 |
| 39 | 170 | 2400 | 16547 | 0.41/4.75/80 | 25 | 0.50 | 2.00% | 29.03 | 84.59 | 4.72 | 6.18 | 3.14 | 0.77 | 0.59 | 0.00 |
| 40 | 170 | 2400 | 16547 | 0.41/4.75/70 | 25 | 0.50 | 1.75% | 28.51 | 85.19 | 4.98 | 5.76 | 2.66 | 0.82 | 0.59 | 0.00 |
| 41 | 170 | 2400 | 16547 | 0.41/4.75/60 | 25 | 0.50 | 1.50% | 26.77 | 87.92 | 3.95 | 5.05 | 2.52 | 0.56 | 0.00 | 0.00 |
| 42 | 170 | 2000 | 13790 | 0.41/4.75/60 | 25 | 0.50 | 1.50% | 41.75 | 73.63 | 9.92 | 8.50 | 3.63 | 2.78 | 1.53 | 0.00 |
| 43 | 176 | 2000 | 13790 | 0.41/4.75/60 | 25 | 0.50 | 1.50% | 49.08 | 69.40 | 12.79 | 7.83 | 3.30 | 4.08 | 2.15 | 0.46 |
| 44 | 176 | 2400 | 16547 | 0.41/4.75/60 | 25 | 0.50 | 1.50% | 38.01 | 82.78 | 6.60 | 5.98 | 2.57 | 1.40 | 0.67 | 0.00 |
| 45 | 186 | 2400 | 16547 | 0.41/4.75/60 | 25 | 0.50 | 1.50% | 57.46 | 73.18 | 13.63 | 6.19 | 1.74 | 3.69 | 1.30 | 0.27 |
| 46 | 160 | 2400 | 16547 | 0.41/4.75/60 | 25 | 0.50 | 1.50% | 14.32 | 92.94 | 1.76 | 3.61 | 1.68 | 0.00 | 0.00 | 0.00 |
| 47 | 160 | 2600 | 17926 | 0.41/4.75/60 | 25 | 0.50 | 1.50% | 11.66 | 93.13 | 1.50 | 3.25 | 2.12 | 0.00 | 0.00 | 0.00 |
| 48 | 180 | 2400 | 16547 | 0.41/4.75/80 | 25 | 0.50 | 1.50% | 47.18 | 79.20 | 9.15 | 6.09 | 2.32 | 2.22 | 1.02 | 0.00 |
| 49 | 180 | 2400 | 16547 | 0.41/7.60/94 | 40 | 0.50 | 1.50% | 38.87 | 81.46 | 8.79 | 4.96 | 1.87 | 2.26 | 0.66 | 0.00 |
| 50 | 180 | 2600 | 17926 | 0.41/4.75/60 | 25 | 0.50 | 1.50% | 40.71 | 82.45 | 7.67 | 5.74 | 2.03 | 1.46 | 0.65 | 0.00 |
| 53 | 170 | 2600 | 17926 | 0.41/4.75/60 | 25 | 0.50 | 1.50% | 24.78 | 88.05 | 3.96 | 5.09 | 2.40 | 0.50 | 0.00 | 0.00 |
| 52 | 160 | 2400 | 16547 | 0.41/2.28/30 | 12 | 0.50 | 1.50% | 18.20 | 86.01 | 2.75 | 5.94 | 4.75 | 0.00 | 0.55 | 0.00 |
| 53 | 170 | 2400 | 16547 | 0.41/2.28/30 | 12 | 0.50 | 1.50% | 35.34 | 81.78 | 4.94 | 7.67 | 4.09 | 0.67 | 0.85 | 0.00 |
| 54 | 180 | 2400 | 16547 | 0.62/7.19/90 | 25 | 0.78 | 1.50% | 34.64 | 79.67 | 8.37 | 6.18 | 2.69 | 2.23 | 0.87 | 0.00 |
| 55 | 180 | 2400 | 16547 | 0.41/2.28/30 | 32 | 0.50 | 1.50% | 56.29 | 72.32 | 11.21 | 9.45 | 3.00 | 2.30 | 1.72 | 0.00 |
| 58 | 174 | 2400 | 16547 | 0.41/2.28/30 | 32 | 0.50 | 1.50% | 44.40 | 77.26 | 7.27 | 9.08 | 3.87 | 1.30 | 1.21 | 0.00 |
| 59 | 172 | 2400 | 16547 | 0.41/2.28/30 | 32 | 0.50 | 1.50% | 38.06 | 79.80 | 6.32 | 8.19 | 3.70 | 0.97 | 1.02 | 0.00 |
| 60 | 165 | 2400 | 16547 | 0.41/2.28/30 | 12 | 0.50 | 1.50% | 26.04 | 82.96 | 4.06 | 7.16 | 4.60 | 0.45 | 0.77 | 0.00 |
| 61 | 165 | 2400 | 16547 | 0.41/4.75/60 | 25 | 0.50 | 1.50% | 18.83 | 90.63 | 2.69 | 4.30 | 2.38 | 0.00 | 0.00 | 0.00 |
| 62 | 170 | 2400 | 16547 | 0.41/7.60/94 | 40 | 0.50 | 1.50% | 21.68 | 91.43 | 3.29 | 3.53 | 1.75 | 0.00 | 0.00 | 0.00 |
| 63 | 170 | 2400 | 16547 | 0.21/2.44/31 | 25 | 0.25 | 1.50% | 38.52 | 81.31 | 7.63 | 6.64 | 2.34 | 1.37 | 0.72 | 0.00 |
| 64 | 190 | 2400 | 16547 | 0.41/7.60/94 | 40 | 0.50 | 1.50% | 54.31 | 74.02 | 14.94 | 4.50 | 1.13 | 4.35 | 0.72 | 0.34 |
| 65 | 160 | 2400 | 16547 | 0.21/2.44/31 | 25 | 0.25 | 1.50% | 23.35 | 88.81 | 3.21 | 4.90 | 3.07 | 0.00 | 0.00 | 0.00 |
| 66 | 169 | 2400 | 16547 | 0.21/2.44/31 | 25 | 0.25 | 1.50% | 40.49 | 80.72 | 8.07 | 6.66 | 2.35 | 1.39 | 0.81 | 0.00 |
| 67 | 180 | 2400 | 16547 | 0.21/2.44/31 | 25 | 0.25 | 1.50% | 59.30 | 72.19 | 14.81 | 6.64 | 1.49 | 3.44 | 1.17 | 0.27 |
| 68 | 170 | 2400 | 16547 | 0.62/7.19/90 | 25 | 0.75 | 1.50% | 20.72 | 88.54 | 3.70 | 4.67 | 2.48 | 0.61 | 0.00 | 0.00 |
| 69 | 190 | 2400 | 16547 | 0.62/7.19/90 | 25 | 0.75 | 1.50% | 49.36 | 69.15 | 15.38 | 5.86 | 2.18 | 5.33 | 1.65 | 0.45 |
| 70 | 170 | 2400 | 16547 | 0.31/3.57/45 | 25 | 0.38 | 1.50% | 29.53 | 86.50 | 4.83 | 5.40 | 2.11 | 0.71 | 0.45 | 0.00 |
| 71 | 180 | 2400 | 16547 | 0.31/3.57/45 | 25 | 0.38 | 1.50% | 53.26 | 74.17 | 12.58 | 6.59 | 1.89 | 1.26 | 1.28 | 0.23 |
| 72 | 160 | 2400 | 16547 | 0.31/3.57/45 | 25 | 0.38 | 1.50% | 14.99 | 91.13 | 2.30 | 4.08 | 2.49 | 0.00 | 0.00 | 0.00 |
| 73 | 160 | 2400 | 16547 | 0.41/7.60/94 | 40 | 0.50 | 1.50% | 10.35 | 96.24 | 1.36 | 2.40 | 0.00 | 0.00 | 0.00 | 0.00 |
| 74 | 170 | 2400 | 16547 | 0.41/4.75/50 | 25 | 0.50 | 1.25% | 26.05 | 87.65 | 4.19 | 5.17 | 2.33 | 0.65 | 0.00 | 0.00 |
| 76 | 177 | 2400 | 16547 | 0.41/4.75/60 | 25 | 0.50 | 1.50% | 36.70 | 83.34 | 6.80 | 5.59 | 2.27 | 1.38 | 0.62 | 0.00 |
| 77 | 176 | 2400 | 16547 | 0.41/4.75/60 | 25 | 0.50 | 1.50% | 34.58 | 84.19 | 6.41 | 5.31 | 2.23 | 1.29 | 0.56 | 0.00 |
| 78 | 176 | 2400 | 16547 | 0.41/4.75/50 | 25 | 0.50 | 1.25% | 35.69 | 83.18 | 6.86 | 5.73 | 2.20 | 1.48 | 0.55 | 0.00 |
| 79 | 176 | 2400 | 16547 | 0.41/4.75/40 | 25 | 0.50 | 1.00% | 35.77 | 82.81 | 6.94 | 5.66 | 2.41 | 1.57 | 0.61 | 0.00 |
| 80 | 176 | 2400 | 16547 | 0.41/4.75/30 | 25 | 0.50 | 0.75% | 35.04 | 84.85 | 6.80 | 5.47 | 0.99 | 1.49 | 0.41 | 0.00 |
| 81 | 176 | 2400 | 16547 | 0.41/4.75/20 | 25 | 0.50 | 0.50% | 34.87 | 82.97 | 7.00 | 5.61 | 2.05 | 1.70 | 0.67 | 0.00 |
| 82 | 176 | 2400 | 16547 | 0.41/4.75/10 | 25 | 0.50 | 0.25% | 34.66 | 79.94 | 8.47 | 5.68 | 2.76 | 2.33 | 0.84 | 0.00 |
| 83 | 179 | 2400 | 16547 | 0.41/4.75/30 | 25 | 0.50 | 0.75% | 38.82 | 80.77 | 8.68 | 5.53 | 2.12 | 2.25 | 0.64 | 0.00 |
| 84 | 173 | 2400 | 16547 | 0.41/2.28/15 | 12 | 0.50 | 0.75% | 35.07 | 82.12 | 5.70 | 7.22 | 3.36 | 0.87 | 0.73 | 0.00 |

TABLE 1-continued

| | conditions | | | reactants | | | | | | | | | | |
|---|---|---|---|---|---|---|---|---|---|---|---|---|---|---|
| Example Number | Reactor Temperature °C. | pressure psig | pressure kPa | MEA/NH$_3$/H$_2$ ml/min | molar ratio NH$_3$/MEA | LHSV | H$_2$ mole % of total feed | MEA % conversion | SELECTIVITY In mole % (based on MEA converted) | | | | | |
| | | | | | | | | | EDA | PIP | DETA | AEEA | AEP | TETA | THPA |
| 85 | 173 | 2400 | 16547 | 0.41/2.28/30 | 12 | 0.50 | 1.50% | 37.47 | 80.85 | 5.94 | 7.73 | 3.72 | 0.90 | 0.86 | 0.00 |
| 86 | 175 | 2400 | 16547 | 0.21/3.87/24 | 40 | 0.25 | 0.75% | 45.82 | 82.95 | 8.62 | 4.75 | 1.37 | 1.95 | 0.37 | 0.00 |
| 87 | 172 | 2400 | 16547 | 0.21/3.87/24 | 40 | 0.25 | 0.75% | 40.07 | 84.54 | 7.01 | 4.86 | 1.68 | 1.47 | 0.43 | 0.00 |
| 88 | 171 | 2400 | 16547 | 0.21/3.87/24 | 40 | 0.25 | 0.75% | 38.90 | 85.15 | 6.45 | 4.94 | 1.68 | 1.38 | 0.40 | 0.00 |
| 89 | 175 | 2400 | 16547 | 0.38/6.96/43 | 40 | 0.45 | 0.75% | 30.02 | 84.94 | 6.59 | 4.44 | 1.99 | 1.65 | 0.39 | 0.00 |
| 90 | 181 | 2400 | 16547 | 0.38/6.96/43 | 40 | 0.45 | 0.75% | 38.23 | 78.14 | 10.62 | 4.97 | 2.18 | 3.26 | 0.84 | 0.00 |
| 91 | 170 | 2400 | 16547 | 0.41/4.75/100 | 25 | 0.50 | 2.50% | 20.04 | 89.61 | 3.61 | 4.79 | 1.98 | 0.00 | 0.00 | 0.00 |
| 92 | 180 | 2400 | 16547 | 0.83/15.46/95 | 40 | 1.00 | 0.75% | 25.22 | 85.68 | 6.88 | 3.93 | 1.64 | 1.87 | 0.00 | 0.00 |
| 93 | 180 | 2400 | 16547 | 0.62/11.6/71 | 40 | 0.75 | 0.75% | 28.54 | 87.75 | 5.57 | 3.99 | 1.38 | 1.30 | 0.00 | 0.00 |
| 94 | 186 | 2400 | 16547 | 0.62/11.6/71 | 40 | 0.75 | 0.75% | 36.57 | 83.85 | 8.61 | 4.16 | 1.02 | 2.36 | 0.00 | 0.00 |
| 95 | 175 | 2400 | 16547 | 0.29/5.41/67 | 40 | 0.35 | 1.50% | 32.60 | 87.63 | 5.64 | 4.44 | 1.21 | 1.08 | 0.00 | 0.00 |
| 96 | 179 | 2400 | 16547 | 0.29/5.41/67 | 40 | 0.35 | 1.50% | 39.24 | 84.44 | 8.13 | 4.63 | 1.11 | 1.69 | 0.00 | 0.00 |
| 97 | 178 | 2400 | 16547 | 0.29/5.41/33 | 40 | 0.35 | 0.75% | 38.23 | 84.64 | 7.99 | 4.51 | 1.14 | 1.73 | 0.00 | 0.00 |
| 98 | 184 | 2400 | 16547 | 0.41/7.80/94 | 40 | 0.50 | 1.50% | 40.37 | 82.15 | 9.55 | 4.74 | 0.93 | 2.31 | 0.32 | 0.00 |
| 99 | 179 | 2400 | 16547 | 0.41/2.28/15 | 12 | 0.50 | 0.75% | 44.46 | 78.18 | 8.73 | 8.25 | 2.48 | 1.51 | 0.85 | 0.00 |

Excess ammonia is used to ensure that EDA is the predominant product in the reaction of MEA with NH$_3$. The literature indicates that an NH$_3$/MEA molar ratio of about 20–25 is necessary in a typical commercial plant. A broad ratio range of 10 to 40 is covered in Table 1. This covers the range from a high ratio, considered uneconomical due to high ammonia recycle, to a low ratio where performance is thought to be unsatisfactorily poor. However, with the catalyst of the invention, performance is satisfactory at the lower ratios.

EXAMPLE 2: ILLUSTRATING THE EFFECTS OF Ni/Cu WEIGHT RATIOS

The procedure of Example 1 is repeated except that 22.55 g and 5.64 g of Cu(NO$_3$)$_2$.2.5H$_2$O are added to the starting solution. The resulting Ni/Co/Cu/Re/B catalysts have a Ni/Cu weight ratios of 1.7 & 6.8, respectively with other weight ratios the same as in Example 1. The results of using these catalysts are listed in Table 2.

The data in Table 2 shows that a catalyst having a 6.8 weight ratio of Ni:Cu is similarly effective in the conversion of MEA as the same catalyst having a weight ratio of 1.7, but gives better selectivity for desired product, EDA, and correspondingly less by products.

EXAMPLE 3: ILLUSTRATING THE EFFECT OF RUTHENIUM

The procedure of Example 1 is repeated except that after all starting solution is impregnated on to the support and thoroughly dried, a 100 ml aqueous solution containing 6.32 g of RuCl$_3$.xH$_2$O is poured onto the support and carefully mixed. Then, the support is dried in the oven at 120° C. again with occasional mixing until completely dry. The resulting Ni/Co/Cu/Ru/Re/B catalyst has a Ni/Ru weight ratio of 3.4 and a total metal loading of about 17.8 weight percent. The results of using this catalyst are listed in Table 3.

TABLE 2

| Run | Ni/Cu weight Ratio | Reactor temp. (°C.) | Reactor pressure (psig) | kPa | MEA/NH$_3$/H$_2$ ml/min | NH$_3$/MEA molar ratio | LHSV | MEA conversion % | SELECTIVITY, % (mole) (based on MEA converted) | | | | | | | H$_2$ mole % of total feed |
|---|---|---|---|---|---|---|---|---|---|---|---|---|---|---|---|---|
| | | | | | | | | | EDA | PIP | DETA | AEEA | AEP | TETA | TEPA | |
| 2:1 | 6.8 | 170 | 2400 | 16547 | 0.41/4.75/100 | 25 | 0.5 | 23.61 | 92.07 | 3.90 | 4.03 | 0.00 | 0.00 | 0.00 | 0.00 | 2.50% |
| 2:2 | 6.8 | 180 | 2400 | 16547 | 0.41/4.75/100 | 25 | 0.5 | 43.99 | 83.43 | 9.71 | 4.93 | 0.40 | 1.53 | 0.00 | 0.00 | 2.50% |
| 2:3 | 6.8 | 190 | 2400 | 16547 | 0.41/4.75/100 | 25 | 0.5 | 52.24 | 72.89 | 15.44 | 5.87 | 1.04 | 4.25 | 0.51 | 0.00 | 2.50% |
| 2:4 | 6.8 | 170 | 2400 | 16547 | 0.41/4.75/61 | 25 | 0.5 | 20.78 | 93.18 | 3.57 | 3.25 | 0.00 | 0.00 | 0.00 | 0.00 | 1.50% |
| 2:5 | 6.8 | 180 | 2400 | 16547 | 0.41/4.75/61 | 25 | 0.5 | 35.23 | 83.44 | 8.47 | 5.53 | 0.80 | 1.76 | 0.00 | 0.00 | 1.50% |
| 2:6 | 6.8 | 190 | 2400 | 16547 | 0.41/4.75/61 | 25 | 0.5 | 44.05 | 74.24 | 14.53 | 5.57 | 1.33 | 4.33 | 0.00 | 0.00 | 1.50% |
| 2:7 | 1.7 | 170 | 2400 | 16547 | 0.41/4.75/100 | 25 | 0.5 | 25.61 | 89.43 | 4.82 | 5.00 | 0.76 | 0.00 | 0.00 | 0.00 | 2.50% |
| 2:8 | 1.7 | 180 | 2400 | 16547 | 0.41/4.75/100 | 25 | 0.5 | 40.30 | 74.37 | 13.47 | 5.61 | 1.79 | 4.24 | 0.52 | 0.00 | 2.50% |
| 2:9 | 1.7 | 190 | 2400 | 16547 | 0.41/4.75/100 | 25 | 0.5 | 51.84 | 69.23 | 17.94 | 5.43 | 1.21 | 6.20 | 0.00 | 0.00 | 2.50% |
| 2:10 | 1.7 | 170 | 2400 | 16547 | 0.41/4.75/61 | 25 | 0.5 | 21.66 | 91.69 | 4.01 | 3.72 | 0.59 | 0.00 | 0.00 | 0.00 | 1.50% |
| 2:11 | 1.7 | 180 | 2400 | 16547 | 0.41/4.75/61 | 25 | 0.5 | 36.47 | 80.64 | 10.48 | 5.23 | 1.07 | 2.58 | 0.00 | 0.00 | 1.50% |
| 2:12 | 1.7 | 190 | 2400 | 16547 | 0.41/4.75/61 | 25 | 0.5 | 45.15 | 67.25 | 18.25 | 5.27 | 1.89 | 6.83 | 0.51 | 0.00 | 1.50% |

TABLE 3

| Run # | Reactor Temp. (°C.) | Reactor pressure (psig) | Reactor pressure (kPa) | MEA/ NH₃/H₂ ml/min | NH₃/MEA molar ratio | LHSV | MEA Conversion % | SELECTIVITY, % (mole) (based on MEA converted) | | | | | | H₂ mole % of Total feed |
|---|---|---|---|---|---|---|---|---|---|---|---|---|---|---|
| | | | | | | | | EDA | PIP | DETA | AEEA | AEP | TETA | TEPA | |
| 3:1 | 160 | 2400 | 16547 | 0.41/4.75/193 | 25 | 0.5 | 16.36 | 90.28 | 1.90 | 5.67 | 2.14 | 0.00 | 0.00 | 0.00 | 4.70% |
| 3:2 | 170 | 2400 | 16547 | 0.41/4.75/193 | 25 | 0.5 | 33.81 | 81.29 | 4.92 | 9.21 | 2.57 | 1.23 | 0.78 | 0.00 | 4.70% |
| 3:3 | 185 | 2400 | 16547 | 0.41/4.75/193 | 25 | 0.5 | 60.46 | 69.84 | 11.99 | 9.60 | 1.54 | 4.57 | 2.47 | 0.00 | 4.70% |
| 3:4 | 160 | 2400 | 16547 | 0.41/4.75/100 | 25 | 0.5 | 14.46 | 92.84 | 1.65 | 3.88 | 1.64 | 0.00 | 0.00 | 0.00 | 2.50% |
| 3:5 | 175 | 2400 | 16547 | 0.41/4.75/100 | 25 | 0.5 | 40.77 | 80.41 | 6.72 | 7.79 | 2.10 | 2.01 | 0.97 | 0.00 | 2.50% |
| 3:6 | 185 | 2400 | 16547 | 0.41/4.75/100 | 25 | 0.5 | 59.79 | 68.65 | 13.45 | 8.10 | 1.48 | 5.57 | 2.76 | 0.00 | 2.50% |
| 3:7 | 160 | 2400 | 16547 | 0.41/4.75/61 | 25 | 0.5 | 15.81 | 92.58 | 2.34 | 3.52 | 1.56 | 0.00 | 0.00 | 0.00 | 1.50% |
| 3:8 | 175 | 2400 | 16547 | 0.41/4.75/61 | 25 | 0.5 | 37.47 | 80.32 | 7.17 | 6.57 | 2.33 | 2.17 | 1.45 | 0.00 | 1.50% |
| 3:9 | 185 | 2400 | 16547 | 0.41/4.75/61 | 25 | 0.5 | 55.03 | 72.51 | 11.79 | 6.83 | 2.02 | 4.78 | 2.06 | 0.00 | 1.50% |

The data from these examples suggests that under these conditions, ruthenium in the catalyst of the invention advantageously improves the yield of desirable product (EDA) and reduces the yield of cyclic by-products at higher concentrations of hydrogen (4.7 percent by weight of total feed), but has little effect at lower concentrations of hydrogen.

EXAMPLE 4. ILLUSTRATING OF THE AMINATION OF POLYOL

The catalyst in example 1 is used for the amination of a polybutylene oxide based polyol, which is made from the reaction of butanol, propyleneoxide and butyleneoxide. The molecular weight of this polyol is about 1500. Results and conditions are summarized in Table 4.

TABLE 4

| Example | Reactor Temperature (C) | Reactor Pressure (psig) | Reactor Pressure (kPa) | Polyol/NH₃/H₂ ml/min | % Amination |
|---|---|---|---|---|---|
| 4:1 | 180 | 2400 | 16547 | 0.21/4.75/100 | 63% |
| 4:2 | 180 | 2400 | 16547 | 0.83/4.75/100 | 27% |
| 4:3 | 200 | 2400 | 16S47 | 0.21/4.75/100 | 98% |

This data shows that the catalyst of the invention is effective in the reductive amination of a polyol.

We claim:

1. catalyst comprising rhenium (atomic number 75), nickel, cobalt, boron and copper and/or ruthenium impregnated on a support material, wherein the weight ratio of the nickel to the rhenium is in the range of from 1 to about 30; the weight ratio of the nickel to the cobalt is from about 1 to about 20; the weight ratio of the nickel to the boron is from about 1 to about 20; the weight ratio of the nickel to the copper and/or ruthenium is from about 1 to about 20.

2. The catalyst of claim 1 wherein the total nickel plus rhenium plus cobalt plus copper and/or ruthenium plus boron metal content is at least about 2 percent by weight based on total weight of support material and metal content.

3. The catalyst of claim 2 wherein the total nickel plus rhenium plus cobalt plus copper and/or ruthenium plus boron metal content is at least about 5 weight percent.

4. The catalyst of claim 3 wherein the total nickel plus rhenium plus cobalt plus copper and/or ruthenium plus boron metal content is less than about 51 weight percent.

5. The catalyst of claim 4 wherein the total nickel plus rhenium plus cobalt plus copper and/or ruthenium plus boron metal content is from about 5 to about 30 weight percent.

6. The catalyst of claim 5 wherein the total nickel plus rhenium plus cobalt plus copper and/or ruthenium plus boron metal content is from about 10 to about 16 weight percent.

7. The catalyst of claim 1 which has additional metals in admixture with the nickel, cobalt, copper, and/or ruthenium, rhenium and boron selected from lanthanum, calcium, chromium, molybdenum, magnesium, lithium, sodium, potassium, rubidium, cesium, cerium, iron, silver, zinc, barium, tungsten, uranium, strontium, palladium, titanium, manganese, and rhodium and combinations thereof.

8. The catalyst of claim 1 wherein the support material is impregnated with at least one salt comprising nickel; at least one salt comprising rhenium; at least one salt comprising (cobalt; at least one boron compound; and at least one salt comprising copper and/or ruthenium.

9. The catalyst of claim 1 wherein the Ni/Re weight ratio is from about 1 to about 10; the Ni/Co, Ni/B and Ni/Cu or Ru weight ratios are each independently from about 1 to about 10.

10. The catalyst of claim 9 wherein the Ni/Re weight ratio is from about 2 to about 6; the Ni/Co, Ni/B and Ni/Cu or Ru weight ratios are each independently from about 2 to about 6.

11. The catalyst of claim 1 wherein the support material has a surface area of from about 10 to about 500 square meters per gram.

12. The catalyst of claim 1 wherein the support material is based on at least one of silicon, aluminum, and titanium.

13. The catalyst of claim 12 wherein the support material is based on at least one of silica or alumina.

14. The catalyst of claim 13 wherein the support material is selected from alpha-alumina, silica, silica-alumina, kieselguhrs or diatomaceous earths and silica-titania.

15. The catalyst of claim 14 wherein the support material includes silica.

16. The catalyst of claim 15 wherein the impregnating solution comprises at least one salt comprising anhydrous and hydrated nickelous nitrate [hydrate: $Ni(NO_3)_2.6H_2O$], nickel acetonyl acetate [$Ni(C_5H_7O_2)2$], nickel chloride hexahydrate [$NiCl_2.6H_2O$], nickel acetate tetrahydrate [$(CH_3CO_2)2Ni.4H_2O$], nickel perchlorate hexahydrate [$Ni(ClO_4)2.6H_2O$], or nickel sulfate hexahydrate [$NiSO_4.6H_2O$]; at least one salt comprising ammonium perrhenate [$NH_4ReO_4$], or rhenium paradioxane [$Re_2O_7 3(C_4H_8O_2)$]; at least one salt comprising cobalt nitrate hexahydrate [$(CoNO_3)_2 6H_2O$], cobalt chloride hexahydrate [$CoCl_2.6H_2O$], cobalt chloride hydrate [$CoCl_2.xH_2O$], or cobalt carbonate hydrate [$CoCO_3,xH_2O$]; at least one boron compound comprising boric acid [$H_3BO_3$], or boron oxide [$B_2O_3$]; and at least one salt comprising copper nitrate hydrate [$CuNO_3)_2 H_2O$], copper chloride hydrate [$CuCl_2.xH_2O$], copper chloride dihydrate [$CoCl_2.2H_2O$], copper perchloride hexahydrate [$Cu(ClO_4)_2.6H_2O$] or ruthenium chloride hydrate [$RuCl_3.xH_2O$].

17. A process for preparing a catalyst, said process comprising (i) impregnating a mixture of metals comprising rhenium, cobalt, copper and/or ruthenium, boron and nickel on a support material in weight ratios of Ni/Re of from about 1 to about 30, Ni/Co, Ni/B, Ni/Cu and/or Ru each of from about 1 to about 20; and (ii) activating said catalyst by heating the catalyst in the presence of hydrogen at an effective temperature for a sufficient period of time to make a catalyst active for reductive amination.

18. The process of claim 17 wherein in the activating step, the catalyst is heated to a temperature of from about 150° C. to about 500° C. for about 30 minutes to about 6 hours.

19. The process of claim 17 wherein the catalyst is heated to a temperature of from about 200° C. to about 500° C. for about 45 minutes to about 3 hours.

20. The process of claim 17 additionally comprising a calcinating step involving heating the impregnated support.

21. The process of claim 17 additionally comprising a drying step involving heating the impregnated support.

22. The process of claim 21 wherein the drying step precedes the impregnating step (i).

23. The process of claim 21 wherein the drying step is simultaneous with the impregnating step (i).

24. The process of claim 21 wherein the catalyst is dried during at least one of the calcining or activating step.

* * * * *